United States Patent [19]
Alving et al.

[11] Patent Number: 6,007,838
[45] Date of Patent: *Dec. 28, 1999

[54] PROCESS FOR MAKING LIPOSOME PREPARATION

[75] Inventors: Carl R. Alving, Bethesda; Roberta R. Owens, Silver Spring; Nabila M. Wassef, Potomac, all of Md.

[73] Assignee: The United States of America as represented by the Secretary of the Army, Washington, D.C.

[ * ] Notice: This patent is subject to a terminal disclaimer.

[21] Appl. No.: 08/475,581

[22] Filed: Jun. 7, 1995

[51] Int. Cl.$^6$ .................................................. A61K 9/127
[52] U.S. Cl. .......................... 424/450; 264/4.1; 264/4.3; 428/402.2
[58] Field of Search ................... 424/450, 1.21, 424/9.32, 9.51, 417; 264/4.1, 4.3; 428/402.2; 436/829; 935/54

[56] References Cited

U.S. PATENT DOCUMENTS 5,607,692  3/1997  Ribier et al. ............................ 424/450

FOREIGN PATENT DOCUMENTS 41 24 252  1/1993  Germany.
WO 87/04592  8/1987  WIPO.

OTHER PUBLICATIONS

Conrad et al. "The Influence of Retinal on Complement-ependent Immune Damage to Liposomes," *Biochimica et Biophysica Acta*, 332: 36–46 (1974).

Alving et al. "Novel Vaccines and Adjuvants: Mechanisms to Action," *Aids Research and Human Retroviruses* 10(2): 591–594 (1994).

Wassef et al. "Liposomes as Carriers for Vaccines," *Immunomethods* 4: 217–222 (1994).

Mayhew et al. "Therapeutic Applications of Liposomes," in Liposomes 7: 289–341 (1983).

Alving et al. "Preparation and Use of Liposomes in Immunological Studies," Liposome Technology (2nd Ed.) vol. III (1993) pp. 317–343.

L. S. Rao "Preparation of Liposomes on the Industrial Scale: Problems and Perspectives," in Liposome Technology, vol. I, G. Gregordias, Ed. (1984) pp. 247–257.

*Primary Examiner*—Gollamudi S. Kishore
*Attorney, Agent, or Firm*—Charles H. Harris; John Francis Moran

[57] ABSTRACT

A process for making a liposome preparation comprised of liposomes that contain an encapsulated material is disclosed. The process comprises (A) providing a plurality of portions of a lipid or liposome formulation; (B) hydrating each of the plurality of portions with a solution comprising a material to be encapsulated; and (C) combining each of the plurality of portions to form a single liposome preparation. The liposome preparations can be used for drug delivery or as vaccines.

34 Claims, 1 Drawing Sheet

PROCESS FOR MAKING LIPOSOME PREPARATION

FIELD OF THE INVENTION

This invention relates to a process for making multilamellar liposome preparations, wherein the liposomes encapsulate a material, such as an antigen or drug. The preparations may be used for vaccines or drug delivery.

BACKGROUND OF THE INVENTION

Liposomes have been used as drug carriers for in vivo drug delivery. Liposome-encapsulated drugs have the following advantages:

- the drugs are encapsulated within a relatively impermeable bilayer membrane where the drug is protected from the environment;
- liposomes can be taken up by cells without overt cytotoxic effects, thus enhancing the cellular uptake of the encapsulated material;
- encapsulation alters pharmacokinetics; and
- liposomes are natural, biodegradable and non-toxic. Mayhew et al., "Therapeutic Applications of Liposomes" in Liposomes, M. J. Ostro, ed. (Marcel Dekker, Inc., 1983) pp 289–341. It is believed that these same advantages will be observed when the liposomes encapsulate antigens.

There are several known process for making multilamellar liposome-encapsulated material on an industrial scale. Rao, "Preparation of Liposomes on the Industrial Scale: Problems and Perspectives," in LIPOSOME TECHNOLOGY, Vol. I, G. Gregordias, ed., (CRC Press, 1984) pp.247–257. In the most widely used of these, a thin lipid film (from an organic solvent) is deposited on the walls of a container, an aqueous solution of the material to be encapsulated is added, and the container is agitated. Bangham et al., J. Mol. Biol. 13: 238 (1965). Under the right conditions, this simple process results in the formation of multilamellar vesicles of liposomes trapping the material. Success of this procedure relies heavily on the formation of the thin lipid film, and variation in encapsulation is seen with different methods of agitation.

Belgian Patent No. 866697 describes an alternative method that does not rely on film formation. In this process, an organic solution of lipid is freeze-dried, resulting in a lyophilized product with physical properties that are conducive to easy hydration by an aqueous solution of the material to be encapsulated.

Problems associated with the known methods of production include variability between batches in the amount of material trapped within the liposomes (encapsulation efficiency), the volume of internal trapping space per amount (mg or $\mu$mole) of lipid; the average diameter of individual liposomes, and size heterogeneity. Mayhew et al., supra. For example, Table I of Conrad et al., Biochim. Biophys. Acta 332: 36–46 (1974), shows that a standard deviation in encapsulation efficiency of 12–13% was found between 18 or 8 independently prepared liposome preparations. It is estimated that the range of values between individual preparations varied by about 50%. A low degree of encapsulation and high variation in encapsulation efficiency from batch to batch under otherwise similar conditions has been reported. Rao, supra.

Industrial methods effective at reducing variability in encapsulation efficiency have not heretofore been developed. The high variation in encapsulation efficiency has adverse consequences with respect to large-scale manufacture of liposome preparations for vaccine or drug delivery. Variation makes it virtually impossible to ensure uniformity from batch to batch, and makes quality control difficult.

SUMMARY OF THE INVENTION

It is an object of the present invention to provide a process for preparing liposome preparations wherein the variation in encapsulation efficiency between batches is reduced.

In accordance with this object, one aspect of the present invention provides a process for making a liposome preparation comprised of liposomes that contain an encapsulated material, wherein the process comprises hydrating a lipid or liposome formulation with a solution of the material to be encapsulated, the improvement comprising: (A) providing a plurality of portions of a lipid or liposome formulation; (B) hydrating each of the plurality of portions with a solution comprising a material to be encapsulated; and (C) combining each of the plurality of portions to form a single liposome preparation. The portions may be washed to remove unencapsulated material before they are combined. The material to be encapsulated may be an antigen or a drug, and the preparation may be used in a vaccine.

Another aspect of the present invention provides a process for making a liposome preparation wherein the liposome contains an encapsulated material, comprising the steps of: (A) providing a plurality of portions of a hydrated liposome formulation; (B) lyophilizing each of the plurality of portions; (C) hydrating each of the plurality of portions with a solution comprising a material to be encapsulated; and (D) combining each of the plurality of portions to form a single liposome preparation.

Yet another aspect of the present provides a process for making a liposome preparation wherein the liposome contains an encapsulated material, comprising the steps of: (A) providing a plurality of containers, wherein each container comprises a lipid or liposome formulation; (B) introducing a solution comprising a material to be encapsulated to one of the plurality of containers, thereby forming a liposome suspension; (C) introducing a liposome suspension previously prepared to another of the plurality of containers; and (D) repeating step (C) to form a liposome preparation.

Additional objects and advantages of the invention will be set forth in part in the description that follows, and in part will be obvious from the description, or may be learned by practice of the invention. The objects and advantages may be realized and obtained by means of the processes and compositions particularly pointed out in the appended claims.

DETAILED DESCRIPTION OF THE PREFERRED EMBODIMENTS

Figure 1:
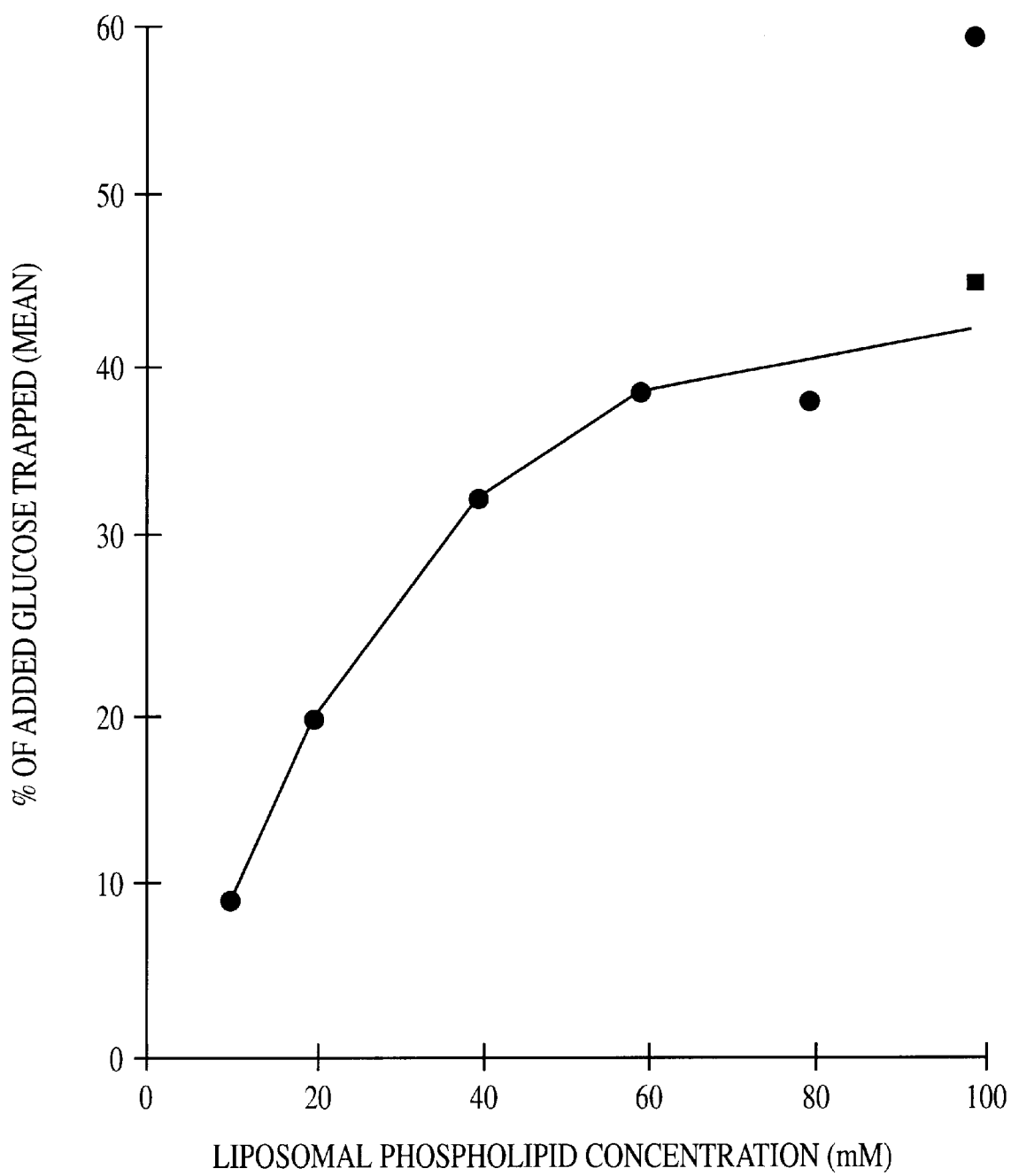
FIG. 1 shows the % of added glucose encapsulated versus liposomal phospholipid concentration when liposome preparations are made according to known procedures (•) and the present invention (■).

There are many possible sources for the variability in encapsulation efficiency observed in the preparation of liposome-encapsulated materials. For example, the size and shape of the vessel used for hydration, temperature, and variations in the thickness of the dried lipid films to be hydrated may contribute to determining the encapsulation efficiency of a given batch. The variation may be a cumulative effect of several or all of these conditions.

The present invention stems from the premise that a major source of variability between batches in the industrial manufacturing of liposomal preparations stems from variability in the hydration step of individual batches, resulting in variation between batches in the amount of material trapped within the liposomes.

To test whether variability at this step is an important determinant in encapsulation efficiency, the following experiment was performed. Dried lipid films were hydrated with decreasing volumes of 0.308 M glucose according to known procedures to form liposome preparations with liposomal phospholipid concentrations of 10 mM, 20 mM, 40 mM, 60 mM, 80 mM, and 100 mM. The •'s in FIG. 1 show the % of added glucose trapped by the liposomes versus liposomal phospholipid concentration for this procedure. A direct relationship was observed for liposomal phospholipid concentrations of 0–40 mM. At higher liposomal phospholipid concentrations, however, encapsulation efficiency differed significantly from the curve. The data point for the 100 mM sample is circled for emphasis.

When a 100 mM preparation was prepared in accordance with one embodiment of the present invention, the encapsulation efficiency was more predictable. In particular, a 0.308 M solution of glucose was added to a container comprising a dry, lipid film, and the container was agitated to hydrate the lipids, resulting in a suspension with a phospholipid concentration of 10 mM. This suspension was added to another container comprising a dry, lipid film, resulting in a suspension with a phospholipid concentration of 20 mM. This process was continued for a total of ten times, resulting in a final liposome preparation with a concentration of 100 mM. The % of glucose trapped by this preparation (see the ■ in FIG. 1) was within the range that would have been predicted based on the data from the 0–40 mM samples discussed above.

This experiment confirmed that a large degree of variation is introduced at the time of hydration. The process of the present invention circumvents this problem, and can be used to prepare liposome preparations with less variation in encapsulation efficiency between batches.

In the process of the present invention, a liposome preparation is made by hydrating a plurality of portions of a lipid or liposome formulation with a solution of the material to be encapsulated and pooling the portions to form the final liposome preparation.

The process of the present invention may be conducted by adapting any procedure for making liposomes, including the known procedures discussed above, such that (A) a plurality of portions of a lipid or liposome formulation is provided, (B) the portions are hydrated with a solution of a material to be encapsulated, and (C) the hydrated portions are combined to form the final liposome preparation.

The portions may be hydrated independently and pooled after each portions has been hydrated to form the final batch of the liposome preparation. Or, in an alternative process, a first portion is hydrated, the resulting suspension is used to hydrate the next portion, the suspension resulting from that hydration is used to hydrate the next portion, and this process is repeated until all portions are hydrated, resulting in the formation of a final batch of the liposome preparation.

In a preferred embodiment, the manufacturing process comprises the following steps: multiple portions of an "empty" aqueous liposome formulation (suspension) are provided. Each portion is lyophilized and hydrated with a solution of a material that is to be encapsulated, resulting in the formation of a plurality of portions of liposomes which have trapped the material. These portions then are pooled to form a single batch, which constitutes the final liposome preparation. Each portion may be washed prior to pooling to remove unencapsulated material.

Alternatively, a plurality of portions of an organic solution of lipids is provided, which each are dried and hydrated with water to form a plurality of "empty" liposome formulations. Each portion is lyophilized and hydrated with a solution of the material that is to be encapsulated. Again, these portions may be washed to remove unencapsulated material. All portions then are combined in a single pool, which constitutes the final liposome preparation.

In yet another alternative procedure, a plurality of portions of a lyophilized, empty, liposome formulation is provided, for example by lyophilizing an empty liposome formulation and aliquoting the lyophilized material into a plurality of portions, or by aliquoting the liposome formulation into portions prior to lyophilization. Each lyophilized portion is hydrated with a solution of the material that is to be encapsulated, and may be washed to remove unencapsulated material. All portions are then combined into a single pool, which constitutes the final liposome preparation.

In yet another embodiment, the method of Bangham et al., supra., is adapted in accordance with the present invention. For example, a plurality of portions of an organic solution of lipids is provided in a plurality of containers, and the organic solvents are evaporated from each portion, for example, by rotary evaporation, resulting in the formation of a thin lipid film on the walls of each container. An aqueous solution of the material to be encapsulated is added to each portion, and the containers are agitated, resulting in the formation of a plurality of portions of liposomes that have trapped the material. These portions then are pooled to form the final liposome preparation.

In another adaptation of this method, a plurality of containers which each have a thin lipid film on the walls thereof are provided. An aqueous solution of a material to be encapsulated is added to one of the containers, and this container is agitated to hydrate the lipid film and form a liposome suspension. This suspension is added to another container which is agitated, and the resulting suspension is added to another container. This process is repeated until all of the lipid films have been hydrated, resulting in the formation of the final liposome preparation.

Other methods of preparing liposome preparations in accordance with the present invention will be apparent to those skilled in the art.

By a "portion of a lipid or liposome formulation" herein is meant an amount of a lipid or liposome formulation. The portion may be in any form, such as a solution, suspension, solid, film or lyophilized powder. By a plurality of portions is meant more than one portion. It is believed that providing at least two portions of a lipid or liposome formulation will achieve the benefits of the present invention.

The plurality of portions provided in accordance with the present invention may be provided in separate containers, such as test tubes, reaction vessels, flasks, or other suitable containers that will be apparent to those skilled in the art. A plurality of portions may be obtained from a plurality of lipid or liposome formulations. Alternatively, a plurality of portions may be prepared by aliquoting a single lipid or liposome formulation into a plurality of containers.

The number of portions of the lipid or liposome formulation that is provided will vary depending on the available starting material, the final preparation, and the laboratory conditions. As discussed above, a minimum of two portions will be provided. The number and size of vessels available, the available volume of material to be encapsulated, the volume of final liposome preparation to be prepared, and the phospholipid concentration needed in the final preparation all may contribute to the decision of the number of portions to prepare.

If a plurality of portions of a liposome formulation is to be lyophilized, it is preferred that the volume of the portion added to each vessel be from about 8% to about 12% of the maximum capacity of the vessel (e.g., for a 50 ml vessel, the liposome aliquot would be 4–6 ml). Use of larger volumes per vessel capacity may result in unpredictable, incomplete lyophilization. The maximum size of the vessel may be determined by the maximum height of vessel which can be accommodated by the particular lyophilizer to be used.

In a preferred embodiment of the present invention, at least 10 portions of the lipid or liposome formulation will be provided, regardless of other considerations. Liposome preparations also have been prepared in accordance with the present invention using 40 to 60 portions to prepare a preparation with a final volume of 100 to 200 ml and a final phospholipid concentration of 50 mM.

Under most circumstances, practical considerations will determine the upper limit of the number of portions provided. For example, if the portions are to be washed by centrifugation, the number of centrifuges available and the capacity of the tubes or bottles used for centrifugation may determine the number of portions provided. In experiments to date, we have prepared, in one day, a single batch of a liposome preparation by dividing a single, empty, aqueous liposome formulation into 200 portions, lyophilizing each portion, hydrating each portion with a solution of antigen, and pooling the portions to form the batch. A larger number of portions also may be provided in accordance with the present invention.

As discussed above, the individual portions of liposomes comprising encapsulated material may be washed before they are pooled into the final batch. Methods of washing to remove unencapsulated material are well-known to those skilled in the art, and will vary with the material that is encapsulated. For example, for some antigens and drugs purification by centrifugation and resuspension will remove nearly all (95% or greater) of the unencapsulated material in the first washing step. In other cases, a second wash is required to achieve at least 95% removal of the unencapsulated material.

For materials that are not soluble at physiological pH, the lipid or liposome formulations are hydrated with a solution of the material to be encapsulated in a buffer at the pH required for solubility. For these preparations, an initial wash may be carried out using the same buffer and pH as was used for hydration, and a second wash may be performed using a buffer at physiological pH. The resulting liposome pellets then may be resuspended in a solution of the buffer at physiological pH for use in the final preparation.

The material to be encapsulated may be, for example, an antigen or a drug. Any antigen or drug may be used, including those which have been encapsulated in liposomes by other methods. Wassef et al. *Immunomethods* 4: 217–222 (1994) Alving et al. *AIDS Res. and Human Retroviruses* 10(2): S91–S94 (1994). For example, two malaria antigens, R32NS1$_{81}$ (SmithKline Beecham, SKF 105154) and NS1$_{81}$RLF (SmithKline Beecham, SKF 107727), recombinant proteins derived from the circumsporozoite protein of the sporozoite stage of the malaria parasite Plasmodium falciparum, have been encapsulated in liposomes in accordance with the method of the present invention and used in clinical trials. Fries et al., *Proc. Natl. Acad. Sci. USA* 89: 358–362 (1992). This vaccine formulation was highly successful as a vaccine formulation and generated high levels of antibodies to malaria antigen in humans.

An antileishmanial drug, sodium stibogluconate (Pentostam®, Wellcome Foundation, Ltd.), also has been encapsulated in liposomes in accordance with the method of the present invention. Alving et al., "Preparation of Liposomes For Use As Drug Carriers in The Treatment of Leishmaniasis," in LIPOSOME TECHNOLOGY, Vol. II, G. Gregordias, ed., (CRC Press, 1984) pp. 55–68. Co-pending U.S. Ser. No. 08/472,780 (Atty. Docket No. 71007/119), the contents of which are incorporated by reference, describes a liposome preparation which encapsulates the HIV envelope protein gp120. This preparation can be prepared in accordance with the present invention.

The final formulation may be packaged for use as a vaccine or drug formulation. Because encapsulation efficiency depends on the nature of the material to be encapsulated, such as the hydrophobicity and charge of the antigen, it cannot be predicted for any particular antigen. The final lipid concentration in a vaccine formulation, therefore, must be empirically derived if a particular dose of antigen per injection volume is desired.

The embodiments of the invention may be further illustrated through examples which show aspects of the invention in detail. These examples illustrate specific elements of the invention and are not to be construed as limiting the scope thereof.

EXAMPLE 1

Manufacturing Protocol for Liposomal R32NS1 Vaccines Containing 1000 μg MPL per Dose The final dosage form was prepared using aseptic precautions. All procedures involving organic solvents were performed in a chemical fume hood.

1. Addition of Lipid Solutions to Evaporation Vessels

Sterile pyrogen-free 100 ml graduated cylinders (graduated in 1 ml) were used to add the lipid solutions to one sterile pyrogen-free acid-washed 2 liter capacity round bottom flask which had a 24/40 ground glass neck. The neck of the round bottom flask was kept covered with aluminum foil (used to maintain the sterility of the flask) except when lipid solutions were being added. The foil was removed just prior to placing the flask on the rotary evaporator.

Added to the flask were:

| Component | ml | mg |
|---|---|---|
| Cholesterol | 85.0 | 4,930 |
| Dimyristoyl phosphatidylcholine (DMPC) (Avanti Polar Lipids, Inc.) | 85.0 | 10,370 |
| Dimyristoyl phosphatidylglycerol (DMPG) (Avanti Polar Lipids, Inc.) | 85.0 | 1,173 |
| Monophosphoryl lipid A (3D-MPL), (Ribi ImmunoChem Research, Inc.) | 85.0 | 680 |
| Total | 340.0 | 17,153 |

2. Rotary Evaporation of the Lipid Solutions

Immediately after the lipid solutions were pipetted into the round bottom flask, it was placed on a rotary evaporator under the following conditions:

| | |
|---|---|
| Water Bath Temperature | 40–45° C. |
| Condenser coils | cooled with running tap water |
| Trap | cooled in ice |
| Angle of rotating flask | approx. 45° |
| Rotation speed | control initially set on 2; reduced to 1 when lipid solution very viscous |
| Vacuum pump | set initially for gauge reading of 200 mbar, then increased to 100 mbar when no bubbling occurs. |

The flask was connected to the evaporator by a sterile glass trap to prevent refluxing of condensed solvent back into the flask. Rotation was continued until all the solvent had evaporated and a thin film of lipid was left on the glass. Once dried (approx. 1 hour) the flask was removed from the evaporator. Immediately after removal, the mouth of the flask was covered with sterile Whatman #541 filter paper which was held in place with a rubber band, placed in a desiccator and further dried under high vacuum (10 mbar) overnight in order to remove any traces of solvent. After drying overnight, the desiccator was closed while under vacuum and kept at 4–60° C. until hydration of the lipid film.

3. Hydration of the Lipid Film

The desiccator was moved to a laminar flow hood, opened and the flask containing the dried lipid film was removed from the desiccator. The filter paper covering the neck of the round bottom flask was replaced by a sterile ground glass stopper. 385 ml of sterile pyrogen-free water for injection (USP) were added to the round bottom flask using sterile pipettes. The ground glass stopper was replaced and the flask was shaken vigorously by hand until all the lipid was removed from the flask wall. The phospholipid concentration at this point, based on the phospholipid added initially and the hydration volume, was approximately 45 mM. The flask of hydrated liposomes was stored at 4–6° C. until the liposomes were bottled for lyophilization.

4. Addition of Hydrated Liposomes to Lyophilization Containers

The flask of hydrated liposomes was decontaminated and transferred to a clean room. After the contents of the flask had come to room temperature, the liposomes were shaken vigorously to ensure homogeneous suspension and a sample was taken for sterility testing. 7.0 ml of hydrated liposomes were pipetted into each of 60 sterile vaccine bottles (60 ml capacity). Grey split stoppers were partially inserted into the bottles. The bottles were placed in the lyophilizer chamber (which opened directly into the clean room), the chamber closed, and the bottles kept at −40° C. for up to 8 hours to freeze the contents.

5. Lyophilization

The freeze-drying cycle was started at −40° C. The temperature was then ramped to 10° C. at the rate of 2.5°/hour. The product was kept at 10° C. for 12–36 hours, then the temperature was adjusted to 20° C. When the freeze-drying cycle was complete, the bottles were removed from the lyophilizer (in the clean room), the stoppers were completely seated, and aluminum seals were applied to each bottle. The bottles were placed in a sterile covered tray and then were transferred from the clean room and stored at 4–6° C. in the dark.

6. Reconstitution of Lyophilized Liposomes with Antigen

R32NS1 antigen (SKF 105154 Lot #U-90055-Z1A, JFM 16843-59) was received as a 190 ml solution at 4.2 mg/ml in acetate buffer, pH 5.5. This solution was dialyzed at 4–6° C. using Spectrapor tubing (M.W. cutoff 3500) previously boiled in 0.2% disodium EDTA for 60 minutes, against 12 liters of PBS, pH 6.5, for 3–6 hours. Following dialysis, the R32NS1 solution was sterilized by filtration through a 0.22 micron filter in a laminar flow hood. The filtered R32NS1 solution was stored at 4–6° C. until used to reconstitute lyophilized liposomes.

The tray of lyophilized liposomes was transferred to a laminar flow hood. The center of each aluminum seal was removed and 1.5 ml of the filtration sterilized dialyzed R32NS1 solution (approximately 4.2 mg/ml) was added by syringe to each bottle to give an approximate phospholipid concentration of 200 mM. The vials were gently shaken to ensure that the lyophilized liposomes were completely wetted, placed back in the covered tray, removed from the hood, and stored at 4–6° C. for 18–72 hours to allow complete reconstitution.

7. Removal of Unencapsulated R32NS1

The tray of reconstituted liposomes was decontaminated and transferred to the clean room. When the liposomes reached room temperature and all the lipid was suspended (no clumps of dried lipid), the aluminum seals were removed from the bottles and 25 ml of filtration sterilized phosphate buffered saline was added by sterile pipette to each bottle. The diluted liposomes were transferred to 46 sterile polycarbonate screw-capped centrifuge tubes (35 ml capacity). The centrifuge tubes (12 at a time) were placed in a sterile SA-600 rotor and the rotor was closed. The rotor was removed from the clean room and placed in a Sorvall RC2b refrigerated high-speed centrifuge. The liposomes were centrifuged for 20 minutes at 14,000 rpm (approx. 30,000×g) at 20–25° C. The rotor was removed from the centrifuge without disturbing the pellet, decontaminated and transferred to the clean room. The centrifuge tubes were removed from the rotor and the supernatant fraction was removed using a sterile Pasteur pipette attached by sterile tubing to a 2 liter sterile vacuum flask connected to a vacuum line. This was repeated until all the tubes were centrifuged.

8. Resuspension of Washed Liposomes

After the supernatant fraction was removed, 1.5 ml of filtration sterilized phosphate buffered saline was added to each centrifuge tube and the liposome pellets were resuspended by hand shaking. The resuspended liposomes were transferred by pipette to a sterile 250 ml graduated cylinder. Each of the centrifuge tubes was rinsed with an additional 1.0 ml phosphate buffered saline and the rinse also transferred to the graduated cylinder. Phosphate buffered saline was added to the pooled liposome pellet to give a final combined volume of 185 ml. Samples were removed for the determination of bulk sterility and antigen encapsulation.

9. Filling Final Containers

The liposome vaccine was dispensed, using aseptic precautions (bottling was performed in a class 100 clean room), into 153 5 ml vaccine bottles at 1.0 ml per bottle. The bottles were stoppered, sealed with aluminum caps, labeled and stored at 4–60° C. Samples were removed for final sterility, safety, pyrogenicity, and potency testing and for determination of antigen encapsulation.

EXAMPLE 2

Manufacturing Protocol for Liposomal R32NS1 Vaccines Containing 100 μg MPL per Dose The final dosage form was prepared using aseptic precautions. All procedures involving organic solvents were performed in a chemical fume hood.

1. Addition of Lipid Solutions to Evaporation Vessels

Sterile glass pipettes (10 ml capacity, graduated in 1/10 ml) and sterile pyrogen-free 100 ml graduated cylinders (graduated in 1 ml) were used to add the lipid solutions to one sterile acid washed 2 liter capacity round bottom flask which had a 24/40 ground glass neck. The neck of the round bottom flask was kept covered with aluminum foil (used to maintain the sterility of the flask) except when lipid solutions were being added. The foil was removed just prior to placing the flask on the rotary evaporator.

Pipetted into the flask were:

| Component | ml | mg |
|---|---|---|
| Cholesterol | 85.0 | 4,930 |
| Dimyristoyl phosphatidylcholine (DMPC) (Avanti Polar Lipids, Inc.) | 85.0 | 10,370 |
| Dimyristoyl phosphatidylglycerol (DMPG) (Avanti Polar Lipids, Inc.) | 85.0 | 1,173 |
| Monophosphoryl lipid A (3D-MPL), (Ribi ImmunoChem Research, Inc.) | 8.5 | 68 |
| Total | 263.5 | 16,541 |

2. Rotary Evaporation of the Lipid Solutions

Immediately after the lipid solutions were pipetted into the round bottom flask, it was placed on a rotary evaporator under the following conditions:

| | |
|---|---|
| Water Bath Temperature | 40–45° C. |
| Condenser coils | cooled with running tap water |
| Trap | cooled in ice |
| Angle of rotating flask | approx. 45° |
| Rotation speed | control initially set on 2; reduced to 1 when lipid solution very viscous |
| Vacuum pump | set initially for gauge reading of 200 mbar, then increased to 100 mbar when no bubbling occurs. |

The flask was connected to the evaporator by a sterile glass trap to prevent ref luxing of condensed solvent back into the flask. Rotation continued until all the solvent had evaporated and a thin film of lipid was left on the glass. Once dried (approx. 1 hour) the flask was removed from the evaporator. Immediately after removal, the mouth of the flask was covered with sterile Whatman #541 filter paper and placed in a desiccator and further dried under high vacuum (10 mbar) overnight in order to remove any traces of solvent. After drying overnight, the desiccator was closed while under vacuum and kept at 4–6° C. until hydration of the lipid film.

3. Hydration of the Lipid Film

The desiccator was moved to a laminar flow hood, opened, and the flask containing the dried lipid film removed from the desiccator. The filter paper covering the neck of the round bottom flask was replaced by a sterile ground glass stopper. 385 ml of sterile pyrogen-free water for injection (USP) were added to the round bottom flask using sterile pipettes. The ground glass stopper was replaced and the flask was shaken vigorously by hand until all the lipid was removed from the flask wall. The phospholipid concentration at this point, based on the phospholipid added initially and the hydration volume, was approximately 44 mM. The flask of hydrated liposomes was stored at 4–6° C. until the liposomes were bottled for lyophilization.

4. Addition of Hydrated Liposomes to Lyophilization Containers

The flask of hydrated liposomes was decontaminated and transferred to a clean room. After the contents of the flask came to room temperature, the liposomes were shaken vigorously to ensure homogeneous suspension and a sample taken for sterility testing. 7.0 ml of hydrated liposomes were pipetted into each of 58 sterile vaccine bottles (60 ml capacity). Grey split stoppers were partially inserted into the bottles. The bottles were placed in the lyophilizer chamber (which opens only into the clean room), the chamber closed, and the bottles kept at −40° C. for up to 8 hours to freeze the contents.

5. Lyophilization

The freeze-drying cycle was started at −40° C. The temperature was then ramped to 10° C. at the rate of 2.5°/hour. The product was kept at 10° C. for 12–36 hours, then the temperature was adjusted to 20° C. When the freeze-drying cycle was complete, the bottles were removed from the lyophilizer (in the clean room), the stoppers were completely seated, and aluminum seals were applied to each bottle. The bottles were placed in a sterile covered tray and then were transferred from the clean room and stored at 4–60° C. in the dark.

6. Reconstitution of Lyophilized Liposomes with Antigen

The tray of lyophilized liposomes was transferred to a laminar flow hood. The center of each aluminum seal was removed and 1.5 ml of the filtration sterilized R32NS1 solution (approx. 4.2 mg/ml, prepared as in Example 1, above) was added by syringe to each bottle to give an approximate phospholipid concentration of 200 mM. The vials were gently shaken to ensure that the lyophilized liposomes were completely wetted, placed back in the sterile covered tray, removed from the hood, and stored at 4–6° C. for 18–72 hours to allow complete reconstitution.

Removal of Unencapsulated R32NS1

The tray of reconstituted liposomes was decontaminated and transferred to the clean room. When the liposomes reached room temperature and all the lipid was suspended (no clumps of dried lipid), the aluminum seals were removed from the bottles and 25 ml of filtration sterilized phosphate buffered saline was added by sterile pipette to each bottle. The diluted liposomes were transferred to 46 sterile polycarbonate screw-capped centrifuge tubes (35 ml capacity). The centrifuge tubes (12 at a time) were placed in a sterile SA-600 rotor and the rotor closed. The rotor was removed from the clean room and placed in a Sorvall RC2b refrigerated high speed centrifuge. The liposomes were centrifuged for 20 minutes at 14,000 rpm (approx. 30,000×g) at 20–25° C. The rotor was removed from the centrifuge without disturbing the pellet, decontaminated and transferred to the clean room. The centrifuge tubes were removed from the rotor and the supernatant fraction was removed using a sterile Pasteur pipette attached by sterile tubing to a 4 liter sterile vacuum flask connected to a vacuum line. This was repeated until all the tubes were centrifuged.

8. Resuspension of Washed Liposomes

After the supernatant fraction was removed, 1.5 ml of filtered, sterilized phosphate buffered saline was added to each centrifuge tube and the liposome pellets were resuspended by hand shaking. The suspended liposomes were transferred by pipette to a sterile 250 ml graduated cylinder. Each of the centrifuge tubes was rinsed with an additional 1.0 ml of sterile phosphate buffered saline and the rinse also transferred to the graduated cylinder. Sterile phosphate buffered saline was added to the pooled liposome pellets to give a final combined volume of 180 ml. Samples were removed for the determination of bulk sterility and antigen encapsulation.

9. Filling Final Containers

The liposome vaccine was dispensed, using aseptic precautions (bottling was performed in a clean room), into 147 5 ml vaccine bottles at 1.0 ml per bottle. The bottles were stoppered, sealed with aluminum caps, labeled and stored at 4–6° C. Samples were removed for final sterility, safety, pyrogenicity, and potency testing and for determination of antigen encapsulation.

EXAMPLE 3

Encapsulation Efficiency of Liposome Preparations from Examples 1 and 2

The two batches of liposomes containing R32NS1 prepared in Examples 1 and 2 above were analyzed to determine the variability in encapsulation efficiency between the batches. The following results were obtained:

| | |
|---|---|
| Example 1 | 20.3% |
| Example 2 | 18.7% |
| Mean (±S.D.) | 19.5 ± 1.1 |
| Deviation from mean | ±0.8% |

These data demonstrate that the variability in encapsulation efficiency of R32NS1 in the two batches was very small, with a deviation from the mean of only ±0.8%. This represents a significant advantage over the 12–13% deviation reported by Conrad et al., supra.

It will be apparent to those skilled in the art that various modifications and variations can be made to the processes and compositions of this invention. Thus, it is intended that the present invention cover the modifications and variations of this invention provided they come within the scope of the appended claims and their equivalents.

What is claimed is:

1. In a process for making a liposome preparation comprised of liposomes that contain an encapsulated material, said process comprising hydrating a lipid or liposome formulation with a solution of a material to be encapsulated, wherein the improvement comprises:

(A) providing a plurality of portions of a dry lipid or dry liposome formulation;

(B) hydrating each of said plurality of portions with a solution comprising said material to be encapsulated; and (C) combining each of said plurality of portions to form a single liposome preparation, thereby forming a liposome preparation comprising liposomes that contain said encapsulated material.

2. The process of claim 1, wherein said material is an antigen.

3. The process of claim 2, wherein said antigen is the HIV antigen gp120.

4. The process of claim 2, wherein said antigen is a malarial antigen selected from the group consisting of $R32NS1_{81}$ and $NS1_{81}RLF$.

5. The process of claim 1, wherein said material is a drug.

6. The process of claim 5, wherein said drug is sodium stibogluconate.

7. The process of claim 1, wherein said preparation is for use in a vaccine.

8. The process of claim 1, further comprising the step of, after step (B) and before step (C), washing each of said plurality of portions to remove material that is not encapsulated.

9. The process of claim 8, wherein said washing comprises centrifuging each of said plurality of portions to form pellets and resuspending said pellets.

10. The process of claim 1, wherein at least 2 portions of said lipid or liposome formulation are provided.

11. The process of claim 1, wherein at least about 10 portions of said lipid or liposome formulation are provided.

12. The process of claim 1, wherein from about 40 to about 60 portions of said lipid or liposome formulation are provided.

13. The process of claim 1, wherein at least about 200 portions of said lipid or liposome formulation are provided.

14. The process of claim 1, wherein said formulation of step (A) is a dry lipid formulation.

15. The process of claim 1, wherein said formulation of step (A) is a dry liposome formulation.

16. The process of claim 1, wherein said step (A) of providing a plurality of portions of a dry liposome formulation comprises:

(i) providing a plurality of portions of a hydrated liposome formulation and (ii) lyophilizing each of said plurality of portions.

17. The process of claim 16, wherein said material is an antigen.

18. The process of claim 16, wherein said material is a drug.

19. The process of claim 16, wherein said preparation is for use in a vaccine.

20. The process of claim 16, wherein at least 2 portions of said hydrated liposome formulation are provided.

21. The process of claim 16, wherein at least about 10 portions of said hydrated liposome formulation are provided.

22. The process of claim 16, wherein from about 40 to about 60 portions of said hydrated liposome formulation are provided.

23. The process of claim 16, wherein at least about 200 portions of said hydrated liposome formulation are provided.

24. The process of claim 16, further comprising, after step (B) and before step (D) (C), washing each of said plurality of portions to remove material that is not encapsulated.

25. The process of claim 24, wherein said washing comprises centrifuging each of said plurality of portions to form pellets and resuspending said pellets.

26. The process of claim 1, wherein:

said step (A) of providing a plurality of portions of a dry lipid or dry liposome formulation comprises providing a plurality of containers, wherein each container comprises a dry lipid or dry liposome formulation; and said step (B) of hydrating each of said plurality of portions and said step (C) of combining each of said plurality of portions comprises:

(i) introducing a solution comprising a material to be encapsulated to one of said plurality of containers, thereby forming a liposome suspension;

(ii) introducing a liposome suspension previously prepared to another of said plurality of containers; and (iii) repeating step (ii) to form a liposome preparation.

27. The process of claim 26, wherein said material is an antigen.

28. The process of claim 26, wherein said material is a drug.

29. The process of claim 26, wherein said preparation is for use in a vaccine.

30. The process of claim 26, wherein at least 2 containers comprising said lipid or liposome formulation are provided.

31. The process of claim 26, wherein at least about 10 containers comprising said lipid or liposome formulation are provided.

32. The process of claim 26, wherein from about 40 to about 60 containers comprising said lipid or liposome formulation are provided.

33. The process of claim 26, wherein at least about 200 containers comprising said lipid or liposome formulation are provided.

34. The process of claim 26, wherein each of said containers comprises a dry lipid film.

* * * * *